United States Patent [19]
Schlein

[11] 3,987,500
[45] Oct. 26, 1976

[54] SURGICALLY IMPLANTABLE TOTAL ANKLE PROSTHESIS

[76] Inventor: Allen P. Schlein, 107 Curtis Terrace, Fairfield, Conn. 06430

[22] Filed: Jan. 28, 1976

[21] Appl. No.: 653,104

[52] U.S. Cl. .................................. 3/1.91; 128/92 C
[51] Int. Cl.[2] ........................................ A61F 1/24
[58] Field of Search ............................ 3/1.9–1.911, 3/1; 128/92 C

[56] References Cited
UNITED STATES PATENTS

| | | | |
|---|---|---|---|
| 3,872,519 | 3/1975 | Giannestras et al. | 3/1 |
| 3,886,599 | 6/1975 | Schlein | 3/1 |
| 3,889,300 | 6/1975 | Smith | 3/1.91 |
| 3,896,502 | 7/1975 | Lennox | 3/1.91 |
| 3,896,503 | 7/1975 | Freeman et al. | 3/1.91 |

*Primary Examiner*—Ronald L. Frinks
*Attorney, Agent, or Firm*—Spencer E. Olson

[57] ABSTRACT

A total ankle prosthesis having a tibial component implanted in the prepared distal end surface of the tibia and a talar component implanted in the prepared proximal end surface of the talus which cooperate to provide an articulated ankle joint, is provided with malleolar components which function as interpositioned membranes for preventing the fibula from rubbing against the bone on the outer side of the talus and/or the talar component and the medial malleous from rubbing against the bone on the inner side of the talus as well as the talar component of the prosthesis. These malleolar components, or shields, are described as associated with a prosthetic device including a distal tibial implant having a convex surface facing the talus, and a proximal talar implant having a convex surface engaging and cooperating with the convex surface of the tibial component, which permits flexion, rotation and sliding movements substantially reproducing the movements of the normal human ankle. In this type of prosthesis, the medial malleolar shield is integral with the tibial component and is shaped to be positioned against the prepared inner surface of the medial malleolus, and the lateral malleolar shield is a separate component having a concave surface and constructed to be implanted in the distal fibula.

8 Claims, 9 Drawing Figures

3,987,500

SURGICALLY IMPLANTABLE TOTAL ANKLE PROSTHESIS

BACKGROUND OF THE INVENTION

The normal human ankle is a joint which is constructed to permit movement in flexion and extension, to provide sliding in the anterior-posterior (A-P) plane, to have a rotation capability and to allow for varus or valgus tiltings. Plantar flexion and dorsiflexion are the major movements of the ankle and may be performed through an angular movement of approximately 20° dorsiflexion and 50° plantar flexion. Rotation is the relative movement of the tibia and the talus about their substantially common vertical axis, the normal rotation limit being approximately 6° to either side, an arc of approximately 12°.

Disease indications of the ankle joint include severe rheumatoid arthritis, avascular necrosis of the talus, degenerative and post traumatic arthritis. Until quite recently, the diseased ankle joint has been treated by local repair procedures, or by obliteration of the joint by fusion, which, of course, renders the ankle stiff and generally immobile. The desirability of replacement of the ankle has been apparent, the first reported use of a total ankle prosthesis known to applicant having been by Buckholz in 1969, and attempts toward developing satisfactory devices have been made in the meantime by several investigators, including the present applicant. Applicant developed a plafond ankle joint replacement device, described in his U.S. Pat. No. 3,886,599, which allowed motion in all of the planes involved in the normal human ankle. This prosthesis consisted of an articulated two-part prosthesis having a convex-to-convex bearing surface provided by an upper metallic portion having a stem adapted for engagement with a prepared distal end of the tibia, and a lower portion formed of high density polyethylene and having a shank adapted for engagement with and connection to a prepared surface of the talus. The confronting convex-bearing surfaces of the upper and lower components provide a line contact which allows them to slide in bi-plane fashion relative to each other, and also allows relative rotation of the tibia and talus about their substantially common vertical axis.

Although the just-described prosthesis has been relatively successful, analysis of the results in patients in which it has been implanted revealed that it was not entirely satisfactory in some cases. In the implantation of the device, debridement of the malleoli and their opposing talar surfaces was included as a part of the operative procedure. However, some malleolar pain often persisted, particularly in cases presenting severe pre-operative angulation at the ankle joint and gross arthritis changes in the malleoli. Applicant also felt that the fibrous scar which developed between the debrided surfaces resulted in diminution in prosthetic motion. Accordingly, the primary object of the present invention is to provide an improved implantable total ankle prosthesis having the advantageous features of his earlier device and which will minimize post-operative malleolar pain and preserve the motion inherent in the design of the prosthesis.

SUMMARY OF THE INVENTION

Briefly, in accordance with the invention, a total ankle prosthesis having a tibial component implanted in the prepared distal end surface of the tibia and a talar component implanted in the prepared proximal end surface of the talus which cooperate to provide a substitute articulated ankle joint is provided with malleolar components or shields which act as interpositioned membranes for preventing pain-causing and bone-deteriorating rubbing of the medial and lateral malleoli against the talar component of the prosthesis and against the bone on the inner and outer surfaces, respectively, of the talus. In the prosthetic device described herein by way of example, the tibial component has a convex surface facing the talus and the medial malleolar shield is in the form of a tab which is integral therewith and is shaped to extend along and to be secured to the prepared inner surface of the medial malleolus. The talar component also has a convex surface engaging and cooperating with the convex surface of the tibial component. The lateral malleolar shield is a separate, relatively thin tab formed of a non-reactive metal alloy and having a concave surface, designed and constructed to be implanted in a prepared cavity in the distal fibula. This prosthesis having, in essence, two articulated bearing components, and medial and lateral malleolar shield components, permits reproduction of essentially all of the movement components of the normal joint, all at the level of the tibio-talar joint of the normal human ankle.

DESCRIPTION OF THE INVENTION

Figure 1:
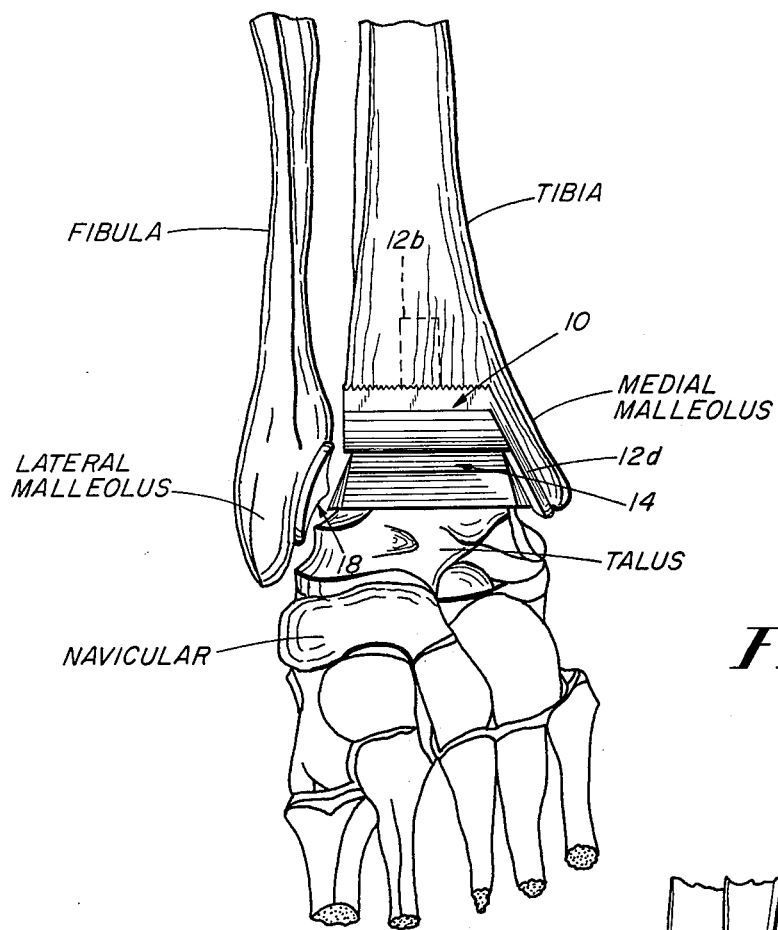
FIG. 1 is a perspective view of the bones forming, and adjacent to, the left human ankle joint, showing the prosthesis provided by the invention in place, in substitution for the human ankle.
Figure 2:
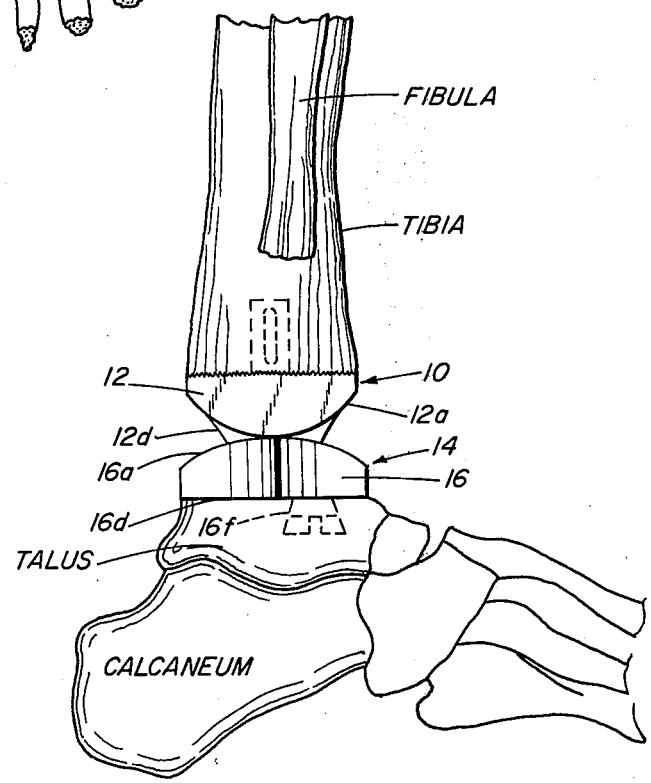
FIG. 2 is a side elevational view of the two parts of the ankle and the tibial and talar components of the prosthesis shown in FIG. 1, with the ankle parts at neutral position.

In FIGS. 1 and 2 the principal parts of the human leg and foot adjacent and forming the foot are shown and labeled, and these being well known to those skilled in the medical and other fine arts, they will not be further described here. These figures also show a presently preferred embodiment of the prosthesis provided by this invention, in operative association with the illustrated parts of the human body. The components are a tibial component which is constructed and intended to be attached to the distal end of the tibia and which, in this illustrative embodiment, has integral therewith a shield which extends downwardly and outwardly along the prepared inner surface of the medial malleolus, a talar component which is constructed and intended to be attached to the talus, and a fibular shield which is constructed and intended to be distally attached to the fibula.

Figure 3:
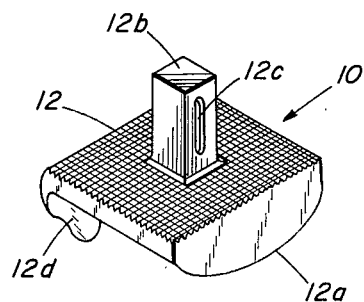
FIG. 3 is a perspective view of the tibial component of the prosthesis shown in FIG. 1.
Figure 3A:
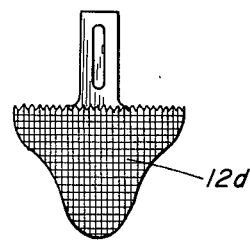
FIG. 3A is an elevational view of the left-hand end of the tibial component as viewed in FIG. 3.

The distal tibial component 10 is formed of a non-reactive metal, such as the chrome-nickel-cobalt alloy known as Vitallium, and as best seen in FIGS. 2, 3 and 3A, consists of a generally rectangularly shaped block 12, the undersurface 12a of which is of convex shape. Integrally joined to and extending perpendicularly upward from approximately the geometric center of the generally rectangular upper surface of the block is a stem 12b of square cross-section, typically 6 mm. on a side, and of a length of about 15 mm., which is adapted to be driven into the distal tibial shaft, there to be held in place by methylmethacrylate cement. The square shape of the stem 12b resists relative rotation between the tibia and the attached component, and continued proper alignment is further ensured by depressions formed in at least two of the vertical surfaces of the stem, one of which is visible at 12c in FIG. 3, and by longitudinal and lateral saw-toothed ridges and grooves formed on the upper surface. The upper surface is somewhat narrower laterally than it is medially, so as to more nearly conform to the shape and area of prepared distal end of the tibia to which it is attached. Integral with and extending downwardly from the medial end of the block 12 and outwardly at an angle of approximately 30° relative to the axis of the stem 12b is a relatively thin shield or tab 12d which is constructed and intended to be secured to and to shield the inner prepared surface of the medial malleolus. Typically, the length of the tab, which is smoothly rounded at its lower end, is about 10 mm. as measured from the lowermost point of the convex surface 12a. The convex surface 12a and the inner surface of the tab 12d are polished to a mirror finish, and the outer surface of the tab has crossed saw-toothed ridges and grooves for receiving cement to increase the adhesion to the medial malleolus.

Figure 5:
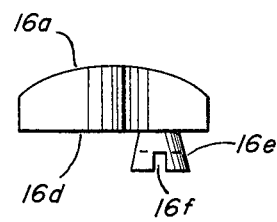
FIG. 5 is a side elevation view of the talar component.
Figure 4:
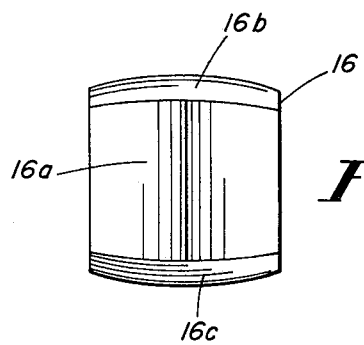
FIG. 4 is a plan view of the upper surface of talar component of the prosthesis shown in FIG. 1.
Figure 6:
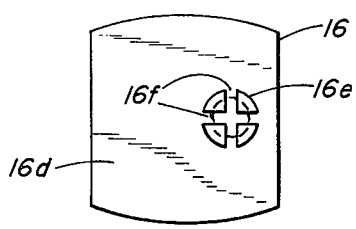
FIG. 6 is a plan view of the underside of the talar component.

The talar component of the prosthesis is designated generally by the reference numeral 14. It is essentially a block 16 formed of a synthetic plastic material such as ultra-high density polyethylene, and has a convex surface 16a which when the component is implanted on a prepared surface of the talus confronts and engages the convex surface 12a of the tibial component. As best seen in FIG. 4, the convex surface is generally rectangular in shape, the radius of curvature of which is typically 25 mm., and the block tapers downwardly and outwardly from the convex surface both medially and laterally as indicated at 16b and 16c. Typically, the block is 9 mm. thick, the front-to-back dimension of the convex surface is 32 mm., and its width is 26 mm. As shown in FIGS. 5 and 6, the undersize of the plastic member is formed to have a planar surface 16d from which depends an integral shank 16e of circular cross-section. The shank has a reverse taper to resist pullout, and its lower end is formed with cross slots 16f to prevent rotation. When implanted, the shank is sunk into a circular hole reamed in the anterior portion of the talar platform, with the surface 16d resting on the platform. The talar component is firmly attached, using a suitable methylmethacrylate cement, the gripping power of which is increased by the reverse taper and the cross slots.

Figure 7:
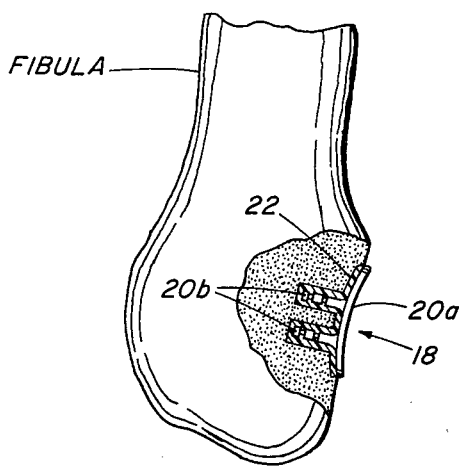
FIG. 7 is a fragmentary side elevational view of the distal end of the fibula, showing the fibular shield in place.
Figure 8:
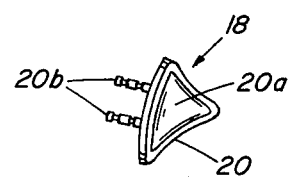
FIG. 8 is a perspective view of the fibular shield.

The lateral malleolar shield of the prosthesis, designated generally by the reference numeral 18, is formed of a non-reactive metal alloy, such as Vitallium, and as best seen in FIG. 8, is a relatively thin, generally triangular-shaped member 20, each side typically being about 17 mm., and has a highly polished concave surface 20a. Integral with and extending from the opposite surface are a pair of fixation prongs 20b. This shield is fitted to a cavity 22 formed in the distal fibula (FIG. 7) and is securely held therein by inserting and cementing the prongs 20b into aligned holes drilled in the fibula. The shield is positioned on the fibula at a point to be below the level of the line of contact of the tibial and talar components of the prosthesis, and generally opposite the medial malleolar shield provided by the tab 12 of the tibial component.

Without going into the full details of the operative procedure, the technique of insertion of the prosthesis will now be described. The prosthesis is usually inserted through a standard anteromedial incision in the joint capsule, retraction of the soft tissues to either side exposing the ankle joint and allowing resection of the distal tibia and medial malleolus so as to accommodate the prosthesis. Approximately one centimeter of bone is removed from the articular surface of the distal tibia, and the inner surface of the medial malleolus is trimmed with an osteotomy saw. The resection includes the posterior lip of the tibia and the cuts are angled to bring the joint into mild valgus.

The ankle is then brought to a neutral position and nine millimeters of bone removed from the talar dome to provide a platform for the talar component of the prosthesis. Utilizing a pre-sized reamer, a hole is then formed in the anterior portion of the talar platform for receiving the shank 16f of the talar component, with care exercised so as not to penetrate the sub-talar joint. The off-center location of the fixation shank permits its insertion at a location on the talar platform at which the risk of penetration into the sub-talar joint is minimized. The sides of the talus are then carefully trimmed with the osteotomy saw to remove all fibroosseous connections between the malleoli and the body of the talus. The talus should both rotate in the ankle joint and piston upward about one-eighth of an inch.

The first component of the prosthesis to be inserted is the fibular shield 18. Using a marketing device and a rotary burr, a cavity is formed in the distal fibia of a depth such that the shield may be fitted flush to the inner cortex as shown in FIG. 7. Next, using a marking guide, vertically aligned holes are drilled in the fibula to receive the fixation prongs 20b. The shield is then cemented into place and all excess cement removed from the joint.

Next, the tibial and talar components, appropriately sized for the patient, are fixed in place; both may be done simultaneously with the ankle held in neutral. The stem of the tibial component, with cement applied, is inserted into a prepared groove in the distal tibia shaft, with cement also applied between the tab 12d and the prepared inner surface of the medial malleolus, and the shank 16f of the talar component is cemented into the hole in the talar platform. All excess polymethylmethacrylate is then removed from the posterior recesses of the ankle joint with a small, curved osteotome by placing manual traction downward in the heel. This is one of the many advantages of the convexity of the mating surfaces of the prosthesis.

The wound is then closed over suction drains and immobilized for 14 to 21 days. At that time, progressive partial weight bearing is allowed and physical therapy instituted to maintain joint motion.

It will be apparent that applicant has provided a prosthetic device for arthoplasty of the human ankle joint which permits implantation with a minimum of disturbance of the ligaments of the ankle, and functions in such a fashion as to emulate the normal motions characteristic of a healthy ankle. The malleolar shields act as interpositioned membranes, the lateral shield keeping the fibula from rubbing against the plastic talar component and the bone on the outer surface of the talus, and the medial shield preventing the medial malleolus from rubbing against the plastic talar component and the bone on the inner surface of the talus, thereby to minimize pain in the malleoli and to protect the bones in the joint against damage.

Although the concept of providing malleolar components has been described and illustrated in the environment of a two-part prosthetic device having convex-to-convex contact which provides a line contact which can slide in the A-P plane and in the plane perpendicular thereto, and which also allows rotation about a vertical axis, their advantages are not limited to this specific type of prosthesis but can, with suitable modification to conform to the structural design of the components of other two-part ankle prosthetic devices, improve their effectiveness including reduction of postoperative pain. Such modifications and variations will now be readily apparent to ones skilled in the art, and are within the intended scope of the invention as defined by the following claims.

I claim:

1. In combination with a two-part prosthetic device for arthoplasty of the human ankle joint including a tibial component for replacing at least a part of the prepared distal end of the tibia and a talar component for replacing at least a part of the prepared proximate surface of the talus, at least a first shield member formed of a metal alloy which is essentially non-reactive with body tissue and constructed and adapted to be attached to the prepared inner surface of the medial malleolus and to extend downwardly between the medial malleolus and the talar component when the latter is implanted, for preventing the medial malleolus from rubbing against said talar component and the bone on the outer surface of the talus.

2. Apparatus in accordance with claim 1, further including a second shield member constructed and adapted to be attached to the prepared distal fibula at a position substantially opposite said first shield member for preventing the fibula from rubbing against said talar component and the bone on the outer surface of the talus.

3. Apparatus in accordance with claim 1, wherein said tibial and talar components each have a convex surface adapted to engage each other along a line contact, wherein said tibial component is formed of a metal alloy which is essentially non-reactive to body tissue, and wherein said first shield member comprises a tab integrally joined to said tibial component and extending downwardly and outwardly when the tibial component is implanted and adapted to be cemented to the prepared inner surface of the medial malleolus.

4. Apparatus in accordance with claim 3, further including a second shield member constructed and adapted to be attached to the prepared distal fibula at a position substantially opposite said tab, said second shield member being formed of a non-reactive metal alloy and having a highly polished, inwardly facing concave surface when implanted.

5. Apparatus in accordance with claim 4, wherein said second shield member is relatively thin and generally triangular-shaped, and has at least one fixation prong integral with and extending from the surface thereof opposite its polished surface adapted to be received in a hole drilled in the distal fibula.

6. Apparatus in accordance with claim 5 wherein said talar component is formed of high density plastic material and includes an integral depending shank offset in the anterior direction from the geometric center of said convex surface and adapted to be received in a hole formed in the anterior portion of the talar platform.

7. Apparatus in accordance with claim 3, wherein said tibial component comprises a generally rectangular block of said alloy, one surface of which has a predetermined radius of curvature defining its convex surface, and the surface which is opposite the convex surface is roughened and has a stem extending therefrom adapted to be received in the tibial shaft, and wherein said tab is joined to and extends downwardly and outwardly from the medial end of the block at an angle of about 30° relative to the axis of said stem.

8. As a new article of manufacture, a tibial prosthesis component for replacing at least a part of the prepared distal end of the tibia, the tibial component comprising a unitary integrally formed device constructed and adapted to be connected to the distal end of the tibia and to serve in lieu of the articulating surface thereof, said tibial component comprising a generally rectangular block of non-reactive metal alloy having a polished downwardly facing bearing surface which is convex, a stem extending upwardly from the upwardly facing surface for implantation in the tibial shaft, and a relatively thin tab joined to and extending downwardly and outwardly from the medial end of the block at a predetermined angle relative to the axis of said stem.

* * * * *